US009816971B2

(12) United States Patent
Jackson et al.

(10) Patent No.: US 9,816,971 B2
(45) Date of Patent: Nov. 14, 2017

(54) CONTROLLABLE INJECTOR SAMPLE DILUTION FOR A LIQUID CHROMATOGRAPHY SYSTEM

(71) Applicant: Waters Technologies Corporation, Milford, MA (US)

(72) Inventors: Michael R. Jackson, Woonsocket, RI (US); Sylvain Cormier, Mendon, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 104 days.

(21) Appl. No.: 14/824,440

(22) Filed: Aug. 12, 2015

(65) Prior Publication Data

US 2016/0069844 A1    Mar. 10, 2016

Related U.S. Application Data

(60) Provisional application No. 62/047,220, filed on Sep. 8, 2014.

(51) Int. Cl.
*G01N 30/20*    (2006.01)
*G01N 30/06*    (2006.01)
(Continued)

(52) U.S. Cl.
CPC ............ *G01N 30/20* (2013.01); *G01N 30/06* (2013.01); *G01N 30/24* (2013.01);
(Continued)

(58) Field of Classification Search
CPC ........ G01N 30/06; G01N 30/20; G01N 30/24; G01N 2030/027; G01N 2030/201; G01N 2030/202
(Continued)

(56) References Cited

U.S. PATENT DOCUMENTS 4,036,063 A * 7/1977 Roof .................. G01N 1/38
137/897
6,790,361 B2 * 9/2004 Wheat ............... B01D 15/166
210/143
(Continued)

FOREIGN PATENT DOCUMENTS

EP      0544988 A1   6/1993
WO     0250531 A2   6/2002

OTHER PUBLICATIONS

Extended Search Report in counterpart European patent application No. 15183268.0, dated Jan. 21, 2016; 6 pages.

*Primary Examiner* — Natalie Huls
*Assistant Examiner* — Monica S Young
(74) *Attorney, Agent, or Firm* — Schmeiser, Olsen & Watts LLP; William G. Guerin

(57) ABSTRACT

Described are a method and a system for injecting a sample into a flow of a liquid chromatography system. The method includes combining a flow of a sample and a flow of a mobile phase to create a diluted sample in the system flow. The volumetric flow rate of the sample is controlled to be at a value that yields a desired dilution ratio for the diluted sample. The particular value at which the volumetric flow rate is maintained can be determined from the desired value of the dilution ratio and the volumetric flow rate of the mobile phase. System embodiments include a syringe that can be used to provide a sample solution at a controllable volumetric flow rate for combination with a high pressure mobile phase.

7 Claims, 4 Drawing Sheets

(51) Int. Cl.
*G01N 30/24* (2006.01)
*G01N 30/02* (2006.01)

(52) U.S. Cl.
CPC . *G01N 2030/027* (2013.01); *G01N 2030/201* (2013.01); *G01N 2030/202* (2013.01)

(58) Field of Classification Search
USPC .......................................................... 73/61.5
See application file for complete search history.

(56) References Cited

U.S. PATENT DOCUMENTS

| | | | |
|---|---|---|---|
| 7,875,175 B2 | 1/2011 | Wheat et al. | |
| 7,909,994 B2 | 3/2011 | Wheat et al. | |
| 8,642,351 B2 * | 2/2014 | Liu | G01N 30/34 210/198.2 |
| 2010/0107742 A1 * | 5/2010 | Liu | G01N 30/34 73/61.56 |
| 2012/0103075 A1 * | 5/2012 | Cormier | F04B 13/02 73/61.55 |
| 2012/0305464 A1 * | 12/2012 | Cormier | G01N 30/20 210/198.2 |
| 2014/0007660 A1 * | 1/2014 | Moeller | G01N 30/20 73/61.56 |
| 2014/0061133 A1 * | 3/2014 | Herman | G01N 30/20 210/659 |
| 2014/0208836 A1 | 7/2014 | Murphy et al. | |
| 2015/0316455 A1 * | 11/2015 | Anderer | B01F 3/0865 73/61.55 |

* cited by examiner

CONTROLLABLE INJECTOR SAMPLE DILUTION FOR A LIQUID CHROMATOGRAPHY SYSTEM

RELATED APPLICATION

This application claims the benefit of the earlier filing date of U.S. Provisional Patent Application No. 62/047,220, filed Sep. 8, 2014 and titled "Controllable Injector Sample Dilution for a Liquid Chromatography System," the entirety of which is incorporated herein by reference.

FIELD OF THE INVENTION

The invention relates generally to sample injection for a liquid chromatography system. More particularly, the invention relates to a method of actively controlling the dilution of a sample at the location of injection into the mobile phase of a liquid chromatography system.

BACKGROUND

Purified compounds are required for testing and analysis protocols applied in many scientific fields. Purification of a compound involves separating a desired component or components from a mixture that contains additional components or impurities. Chromatography methods can be applied to fractionate a mixture into separate components. In liquid chromatography, a sample containing a number of components to be separated is injected into a system flow and directed through a chromatographic column. The column separates the mixture by differential retention into its separate components. The components elute from the column as distinct bands separated in time.

A typical high performance liquid chromatography (HPLC) system includes a pump for delivering a fluid (the "mobile phase") at a controlled flow rate and composition, an injector to introduce a sample solution into the flowing mobile phase, a chromatographic column that contains a packing material or sorbent (the "stationary phase"), and a detector to detect the presence and amount of the sample components in the mobile phase leaving the column. When the mobile phase passes through the stationary phase, each component of the sample typically emerges from the column at a different time because different components in the sample typically have different affinities for the packing material. The presence of a particular component in the mobile phase exiting the column can be detected by measuring changes in a physical or chemical property of the eluent. By plotting the detector signal as a function of time, response "peaks" corresponding to the presence and quantities of the components of the sample can be observed.

Preparative HPLC is a convenient way to isolate and purify a quantity of a compound for further studies or use. Depending on the specific application, preparative separations can be performed using large columns and sample sizes, or may be performed using small columns for smaller volume collection of components. A common distinction between preparative and analytical HPLC is that for preparative HPLC, the sample components are collected after purification, whereas for analytical HPLC, the sample components are simply detected and quantified.

HPLC systems sometimes require that a sample be diluted before the sample is injected into the mobile phase flowing to the chromatography column. The solvent used to dilute the sample may interfere with the ability to obtain a desired chromatographic resolution. Generally, it is preferable to keep a sample focused at the head of the chromatographic column; however, strong solvents can limit the retention of the sample and instead promote the release of the sample as it enters the column. In some separations, the result may be two chromatographic peaks and, in other separations, the sample may simply flow with the solvent through the column.

SUMMARY

In one aspect, a method for injecting a sample into a flow of a liquid chromatography system includes providing a flow of a mobile phase at a first volumetric flow rate and combining a flow of a sample at a second volumetric flow rate and the flow of the mobile phase. The combined flows create a diluted sample having a dilution ratio that is responsive to the first and second volumetric flow rates. The second volumetric flow rate is controlled to a value so that the dilution ratio has a predetermined value.

In another aspect, a system for injecting a sample into a flow of a liquid chromatography system includes a syringe to dispense a sample, a first fluid channel to conduct a mobile phase, a second fluid channel in communication with the syringe to receive the sample, a valve and a control module. The valve has a first port in communication with the first fluid channel, a second port in communication with the second fluid channel, and a third port. The valve has at least two states of operation, wherein when the valve is in a first state, the first port is in communication with the third port and wherein when the valve is in a second state, the first and second ports are in communication with the third port. The control module is in communication with the syringe to control a volumetric flow rate of the sample dispensed from the syringe. The control module is also in communication with the valve to thereby control the state of operation of the valve, wherein the mobile phase conducted through the first fluid channel is dispensed from the third port when the valve is in the first state and wherein the volumetric flow rate of the sample is controlled to a value to obtain a predetermined sample dilution ratio of a diluted sample dispensed from the third port when the valve is in the second state.

In still another aspect, a computer program product for injecting a sample into a flow of a liquid chromatography system includes a computer readable storage medium having computer readable program code. The computer readable program code includes computer readable program code configured to provide a flow of a mobile phase at a first volumetric flow rate. The computer readable program code also includes computer readable program code configured to combine a flow of a sample at a second volumetric flow rate and the flow of the mobile phase, wherein the combined flows create a diluted sample having a dilution ratio that is responsive to the first and second volumetric flow rates and wherein the second volumetric flow rate is controlled to a value so that the dilution ratio has a predetermined value.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Figure 1:
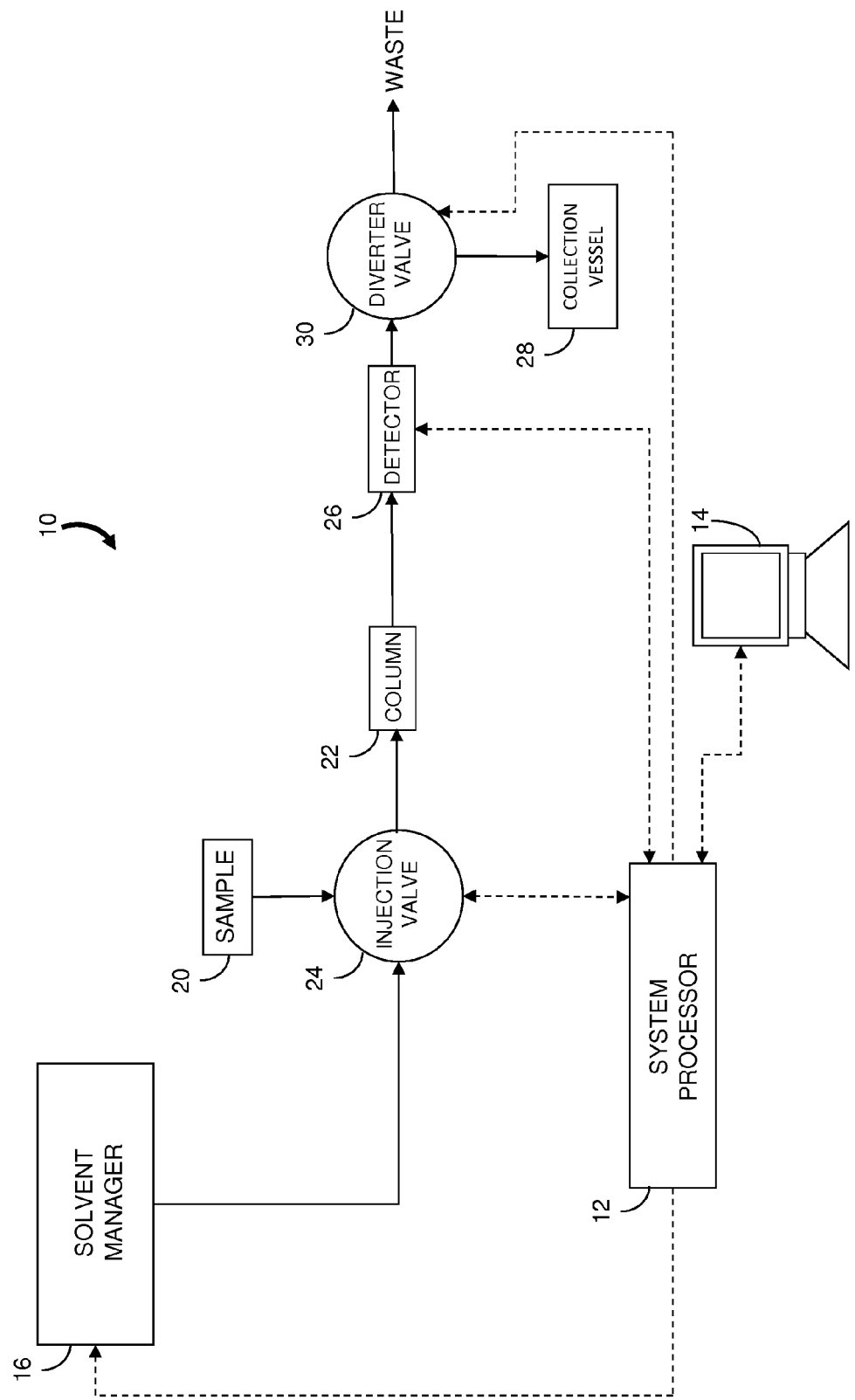
FIG. 1 is a block diagram of a liquid chromatography system that can be used to practice embodiments of the method of the invention.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The mobile phase is a solvent used to dissolve a sample and carry the sample through the stationary phase of a liquid chromatography system. As used herein, the word "sample" refers to a sample solution that contains the sample components to be injected into the system flow of the liquid chromatography system. The sample is typically made available in a sample reservoir or sample container. The sample solution may also include a sample diluent. The mobile phase may be a gradient mobile phase in which the composition of the mobile phase changes with time.

As used herein, a solvent is sometimes referred to as a "strong solvent" or a "weak solvent" to indicate the relative elution strength of the solvent with respect to one or more other solvents. If the mobile phase is a strong solvent, the sample dissolved in the strong solvent will have a greater affinity for the mobile phase than the stationary phase. A strong solvent is generally capable of dissolving a greater quantity of a sample than a weak solvent; however, with the use of a strong solvent there may be a shorter retention time and little or no retention of the sample on the stationary phase. In contrast, if the mobile phase is a weak solvent, the sample dissolved in the weak solvent will have a greater affinity for the stationary phase than the mobile phase. As a result, sample components are better retained on the stationary phase and have longer retention times. By way of non-limiting examples for reversed phase chromatography, solvents composed primarily of methanol, acetonitrile, ethanol, isopropanol or tetrahydrofuran are typically considered strong solvents whereas water is generally considered a weak solvent. By way of non-limiting examples for normal phase chromatography and supercritical fluid chromatography, hexane and heptane are generally considered weak solvents, and methanol, ethanol and water are typically considered strong solvents.

In order for the stationary phase in the chromatographic column to preferentially retain sample components, the mobile phase is initially composed of a weak solvent of sufficiently low or moderate strength to prevent the sample components from simply passing through the column with little or no retention or separation. A gradient mobile phase gradually increases in strength over time to elute the sample components at different times.

In various applications, the sample may be provided in a solution that includes a strong diluent which may interfere with retention of the sample components on the stationary phase. To enable the sample components to be retained, or "focused," at the head of the chromatographic column, it is often desirable to further dilute the sample solution using a weaker solvent although the volume of the diluted sample is thereby increased. The use of the phrase "dilution ratio" is used herein to describe the degree, or amount, of the dilution and means a unit volume contribution of the sample with respect to the number of unit volumes contributed by the one or more diluents.

In brief overview, the invention relates to a method and a system for injecting a sample into a flow of a liquid chromatography system. The method may be used to improve sample loading for a preparative system or to improve chromatographic resolution in an analytical system. The method includes combining a flow of a sample and a flow of a mobile phase to create a diluted sample in the system flow. The volumetric flow rate of the sample is controlled to be at a value that results in a desired dilution ratio for the diluted sample. The particular value at which the volumetric flow rate is maintained can be determined from the desired value of the dilution ratio and the volumetric flow rate of the mobile phase. Various embodiments of the system are based on controlling the volumetric flow rate of a sample solution that is dispensed from a sample syringe and combined with the high pressure mobile phase.

Embodiments of the system described herein allow for controlled dilution of a sample at the location of injection into a pressurized system flow. These embodiments can be used to replace systems that are more complex and have more components. Another advantage is the wide continuous range of dilution ratios that can be realized. The user can reduce or minimize dilution to ensure a tight injection band. Alternatively, the user can use a greater dilution to control the negative effects on chromatographic separations that can occur when using a strong solvent diluent at the sample source. For example, a greater dilution may be preferred when the sample is provided in a strong solvent that would otherwise reduce or eliminate retention of the sample components at the head of the chromatographic column. Conventionally, samples provided in strong solvents are further diluted by a manual addition of a second diluent using a second sample reservoir or container. The ability to dilute the sample at the location of injection into the system flow according to the embodiments described herein eliminates the need for this manual dilution preparation step and avoids the associated potential for human error. Still another advantage is that no changes in the physical components of the system are required to change the dilution ratio. Instead, a user programs a sequence or issues commands through a user interface to change the volumetric flow rate from the sample syringe.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

FIG. 1 is a block diagram of a liquid chromatography system 10 that can be modified to practice embodiments of the method of the invention. The system 10 includes a system processor 12 (e.g., microprocessor and controller) in communication with a user interface device 14 for receiving input parameters and displaying system information to an operator. The system processor 12 communicates with a solvent manager 16 which provides one or more solvents for a mobile phase. For example, the solvent manager 16 may provide a gradient mobile phase. A sample from a sample source 20 is injected into the mobile phase upstream from a chromatographic column 22 at an injection valve 24. The sample source 20 can be a sample reservoir such as a vial or other container that holds a volume of the sample. In some instances, the sample source 20 provides a diluted sample that includes the sample and a diluent. The chromatographic column 22 is coupled to a detector 26 which provides a signal to the system processor 12 that is responsive to various components detected in the eluent from the column 22. After passing through the detector 26, the system flow exits to a waste port; however, when used for fraction collection, a diverter valve 30 is used to direct the system flow to one or more collection vessels 28.

Figure 2:
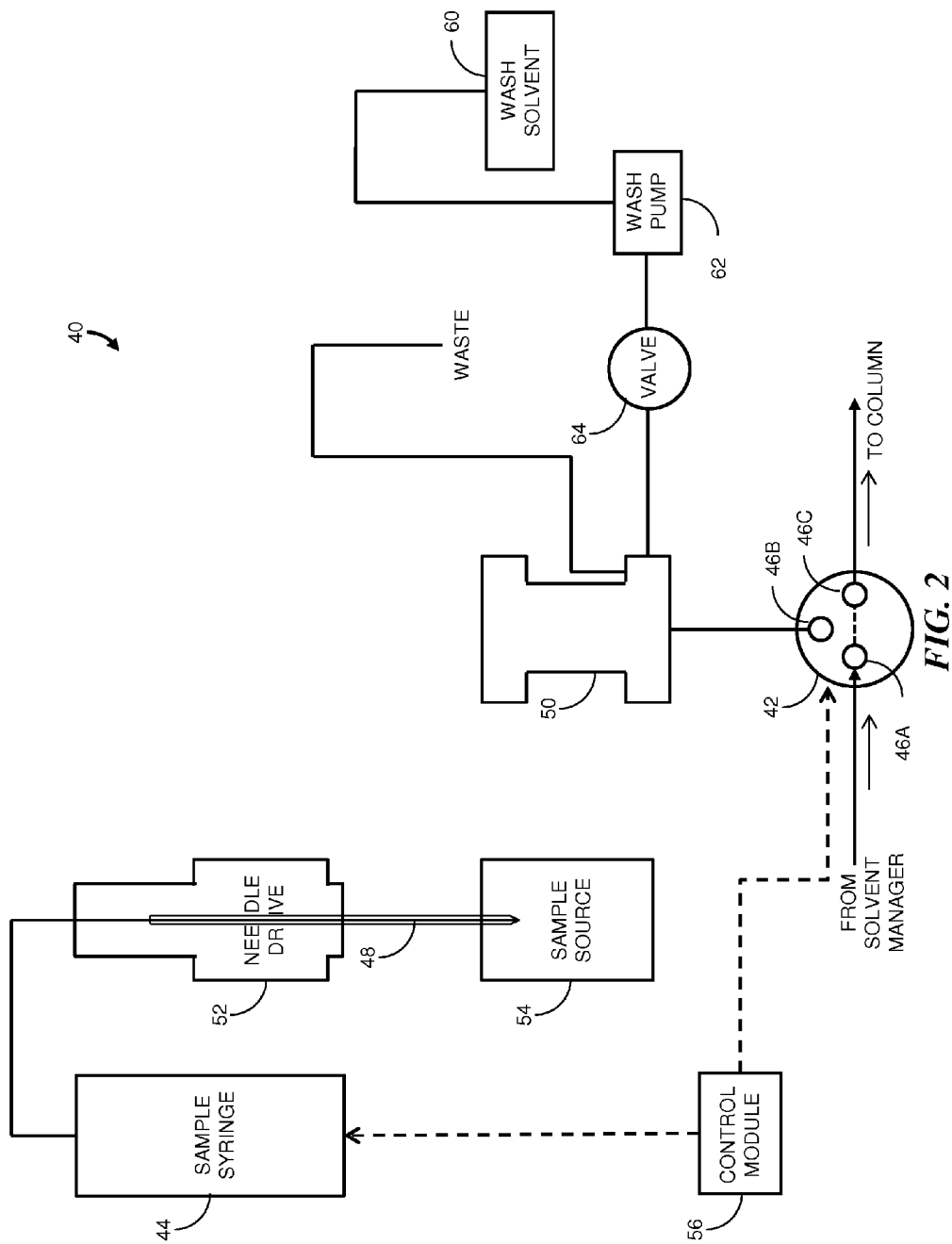
FIG. 2 is a block diagram of an embodiment of a system for injecting a sample into a flow of a liquid chromatography system when the system is configured for loading a sample.

FIG. 2 is a block diagram of an embodiment of a system 40 for injecting a sample into a flow of a liquid chromatography system according to the invention. The system 40 includes a valve 42 having three ports 46A, 46B and 46C (generally 46), a sample syringe 44, a sample needle 48, an injection port 50, a needle drive 52, a sample source 54 and a control module 56.

The sample syringe 44 is adapted for direct fluidic communication with the pressurized system flow of the liquid chromatography system. For example, the sample syringe 44 may be formed as a stainless steel barrel and plunger, and have a stroke that can be accurately controlled for speed and displacement while operating under high system pressures (e.g., 7,000 psi).

One of the ports 46A on the valve 42 communicates with a solvent manager through tubing or another form of conduit to receive a system flow in the form of a mobile phase. A second port 46B is in communication with the injection port 50 and is configured to receive a sample to be injected into the system flow. A third port 46C is in communication with a chromatographic column through tubing or other conduit. The valve 42 is operable in at least two states in which the configurations of liquid flowing through the vale 42 are different. The valve 42 is shown in a first state in which the mobile phase from solvent manager received at port 46A passes through the valve 42 and exits at port 46C. In a second state, the flow of the mobile phase through the valve 42 remains the same; however, the sample provided at port 46B is combined with the mobile phase received at port 46A such that the combined flows exit the valve 42 at port 46C.

The injection valve 42 operates at high system pressures, for example, pressures that may exceed 25,000 psi. In some embodiments, the valve 42 is a rotary shear seal valve. Examples of other types of valves that can operate at sufficiently high pressure and be used as an injection valve include a gate valve, a butterfly valve, a needle valve or a rotary cylinder valve. Although shown as only having three ports 46, it should be recognized that a valve having more than three ports can also be used as long as the valve can be configured to provide the same flow paths and switching capability as the illustrated valve 42.

Control of the injection valve 42 is achieved with the control module 56 and includes the ability to switch the valve 42 between the two states. In various embodiments, the control module 56 may be implemented in a system processor 12 (FIG. 1). In alternative embodiments, the control module 56 is a computer (e.g., personal computer (PC)) or standalone controller that can receive commands or one or more control signals from the system processor 12 or other module.

Figure 3:
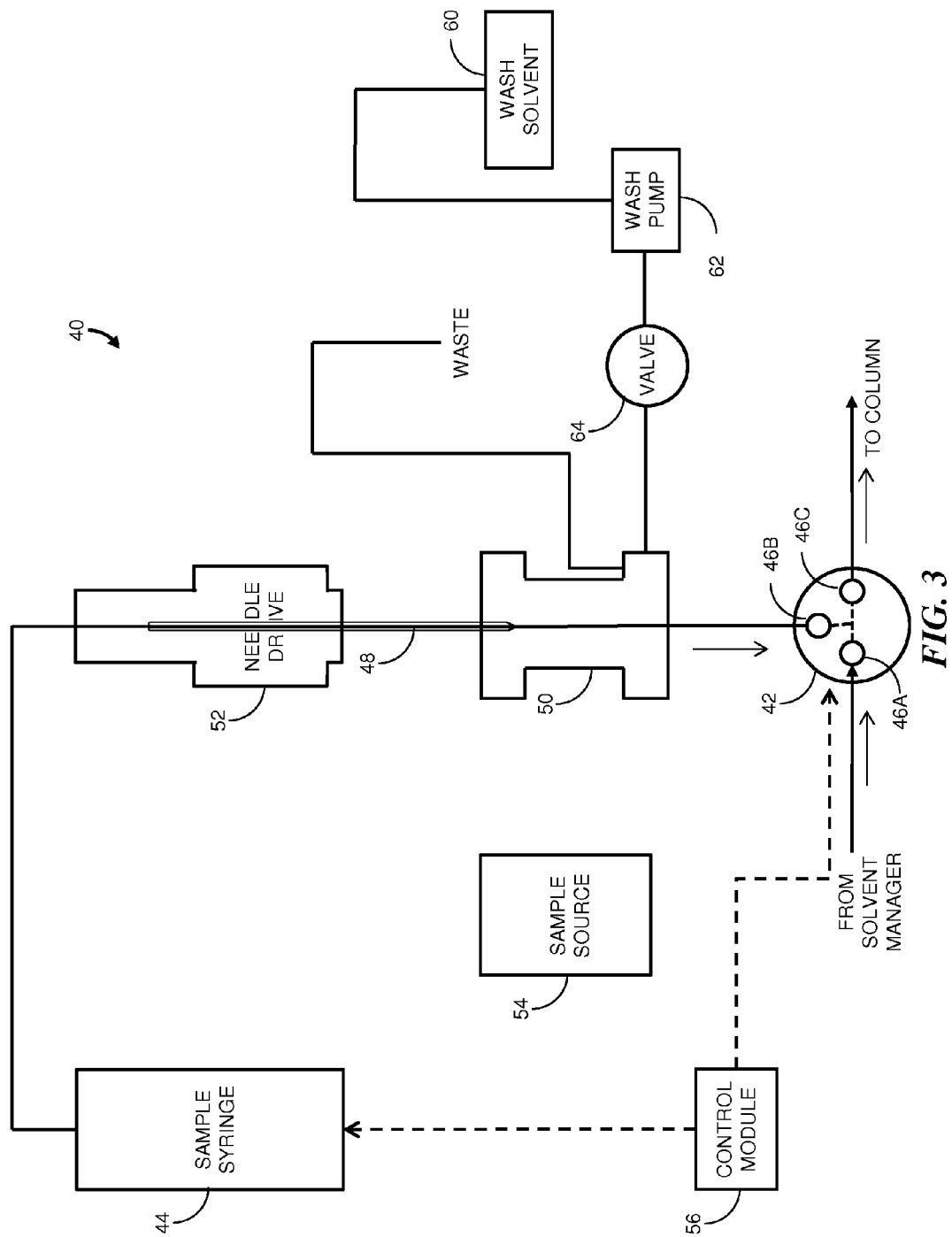
FIG. 3 is a block diagram of the system shown in FIG. 2 when the system is configured for introducing the sample into the mobile phase of the liquid chromatography system.

The needle drive 52 is used to move the sample needle 48 to various positions within the system 40. For example, the needle drive 52 is used to move the tip of the sample needle 48 into position in the sample source 54 (e.g., sample reservoir or sample vial), as illustrated, and can be used to move the sample needle 48 to a position in which the sample needle 48 engages the injection port 50 as shown in FIG. 3.

The control module 56 is also in communication with the sample syringe 44 and is used to control the loading of sample from the sample source 54 into the sample needle 48 and the dispensing of sample from the sample needle 48 into the mobile phase. Sample dilution at the location of injection according to embodiments of the methods and systems described herein generally refers to dilution of the liquid from the sample source by the mobile phase of the chromatography system. If the sample source provides an undiluted sample, the mobile phase is the only diluent. In contrast, if the sample source 54 provides the sample in a sample diluent, the mobile phase is a second diluent that is used to further dilute the raw sample. The control module 56 is used to accurately control the volumetric flow rate of the sample dispensed from the sample needle 48 into the mobile phase.

In various embodiments described herein, the dilution of the sample dispensed from the sample needle 48 into the mobile phase is determined according to the volumetric flow rates of the sample and the mobile phase. It will be recognized that the sample from the sample source may be in a sample diluent and thus there may be a different dilution ratio which is associated with the sample at the sample source 54. The total dilution of the sample is affected by any dilution at the sample source 54 as well as the dilution achieved during injection into the mobile phase.

The illustrated system is shown with a source 60 of a wash solvent that is in communication with the injection port 50 through a wash pump 62 and a wash valve 64. These components are used to wash the fluid path in the injection port 50 and to purge the solvent from the sample needle 48. These operations may be used after completion of a sample injection or before initiating a subsequent sample injection in order to reduce or eliminate cross-contamination that may occur between sample injections for consecutive separations.

Figure 4:
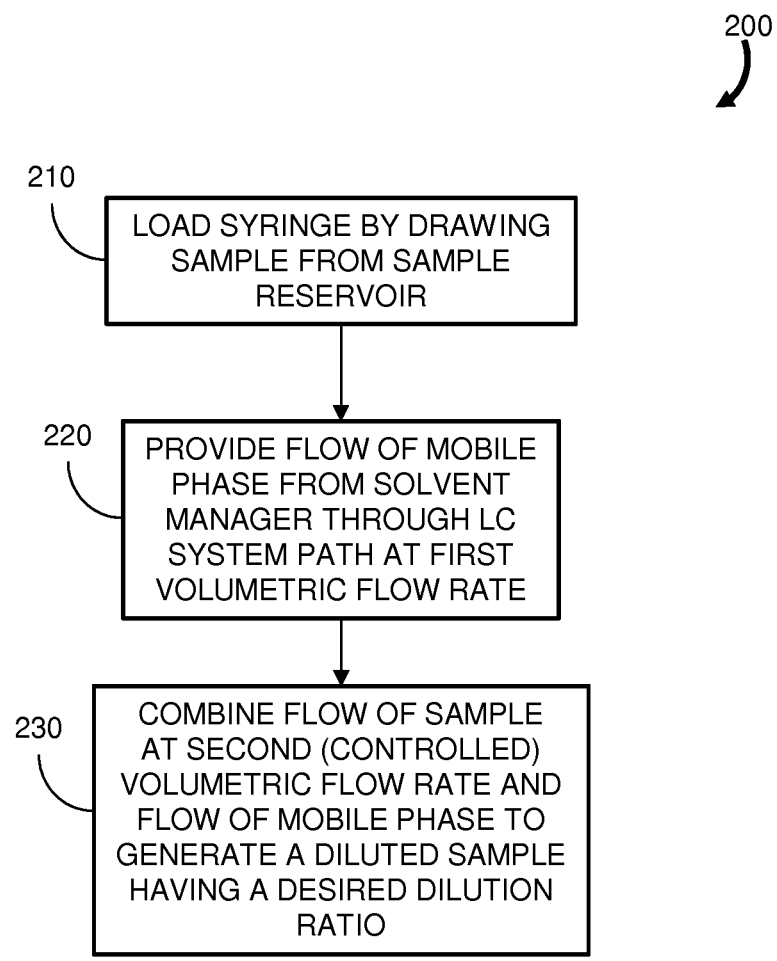
FIG. 4 is a flowchart representation of an embodiment of a method for injecting a sample into a flow of a liquid chromatography system.

Referring to FIG. 2 and also to the flowchart representation of an embodiment of a method 200 for injecting a sample into a flow of a liquid chromatography system as shown in FIG. 4, the sample syringe 44 is loaded (step 210) by acquiring sample from the sample source (e.g., sample reservoir) 54. The volume of sample acquired is determined by the intake stroke of the syringe 44. A flow of mobile phase at a first volumetric flow rate is provided (step 220) through the system path of the liquid chromatography system in advance of and during the sample injection. The needle drive 52 removes the sample needle 48 from the sample source 54 and moves it into the injection port 50 as shown in FIG. 3. Subsequently, the sample syringe 44 is activated by the control module 56 to dispense a flow of the sample into the mobile phase. This combination (step 230) of the two flows creates a diluted sample in the mobile phase. The volumetric flow rate of the sample dispensed from the syringe 44 is controlled to a value that enables the dilution of the sample caused by the combination of the two flows to have the desired dilution ratio. For example, if the volumetric flow rate of the mobile phase is ten times the volumetric flow rate of the sample, the resulting dilution ratio is 1:10 for the liquid dispensed from the sample needle 48. As described above, the total dilution for the raw sample may be greater if the sample reservoir 54 containing the sample also contains a diluent.

The control module 56 can be configured to receive data indicating the desired volumetric flow rate for the sample, for example, from input data provided through a user input device. Alternatively, the user may input a desired dilution ratio at the user input device and the control module 56 (or a processor (not shown) in communication with the control module 56) can determine the corresponding volumetric flow rate for the sample and generate the appropriate signals to control the sample syringe 44.

As will be appreciated by one skilled in the art, aspects of the present invention may be embodied not only as a system or a method, as described above, but also as a computer program product. Accordingly, aspects of the present invention may also take the form of an embodiment combining software and hardware aspects that may all generally be referred to as a system, and as an entirely software embodiment (including firmware, resident software, micro-code, etc.). Furthermore, aspects of the present invention may take the form of a computer program product embodied in one or more computer readable mediums having computer readable program code embodied thereon.

Any combination of one or more computer readable mediums may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific but non-exhaustive examples of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. More generally, as used herein a computer readable storage medium may be any tangible medium that can contain, or store a program for use by or in connection with an instruction execution system, apparatus or device.

Computer program code for carrying out operations for aspects of the present invention, for example, aspects of the method embodiments described above, may be written in any combination of one or more programming languages. The program code may execute entirely on the user's computing system, partly on the user's computing system, as a stand-alone software package, partly on the user's computing system and partly on a remote computing system or entirely on the remote computing system or server. In the latter scenario, the remote computing system may be connected to the user's computing system through any type of network, including a local area network (LAN) or a wide area network (WAN), or the connection may be made to an external computer (for example, through the Internet using an Internet Service Provider).

While the invention has been shown and described with reference to specific embodiments, it should be understood by those skilled in the art that various changes in form and detail may be made therein without departing from the spirit and scope of the invention as recited in the accompanying claims.

What is claimed is:

1. A system for injecting a sample into a flow of a liquid chromatography system, the system comprising:
    a syringe to dispense a sample;
    a first fluid channel to conduct a mobile phase;
    a second fluid channel in communication with the syringe to receive the sample;
    a valve having a first port in communication with the first fluid channel, a second port in communication with the second fluid channel, and a third port, the valve having at least two states of operation, wherein, when the valve is in a first state, the first port is in communication with the third port and wherein, when the valve is in a second state, the first and second ports are in communication with the third port; and
    a control module in communication with the syringe and configured to control a volumetric flow rate of the sample dispensed from the syringe, the control module being in further communication with the valve and configured to control the state of operation of the valve, wherein the mobile phase conducted through the first fluid channel is dispensed from the third port when the valve is in the first state and wherein the combined flow of the mobile phase conducted through the first channel and the flow of the sample conducted through the second channel are dispensed as a diluted sample from the third port when the valve is in the second state, the volumetric flow rate of the sample being controlled to a value to obtain a predetermined sample dilution ratio of the diluted sample.

2. The system of claim 1 wherein the sample includes a diluent.

3. The system of claim 1 wherein the second fluid channel comprises a sample needle.

4. The system of claim 3 further comprising a needle drive coupled to the sample needle and configured to move the sample needle to a position at which the sample needle is loaded with the sample and to a position at which the sample needle is configured to dispense the sample into the valve.

5. The system of claim 3 wherein the second fluid channel comprises an injection port configured to receive the sample needle.

6. The system of claim 1 wherein the control module comprises a first controller in communication with the syringe and a second controller in communication with the valve.

7. The system of claim 1 further comprising a solvent manager in communication with the first fluid channel.

* * * * *